US012727808B2

(12) United States Patent
Mangual-Soto et al.

(10) Patent No.: US 12,727,808 B2
(45) Date of Patent: Sep. 8, 2026

(54) METHOD AND SYSTEM TO MANAGE ADAPTIVE SENSING

(71) Applicant: Pacesetter, Inc., Sylmar, CA (US)

(72) Inventors: Jan O. Mangual-Soto, Rho (IT); Nima Badie, Berkeley, CA (US); Wenwen Li, San Jose, CA (US); Fady Dawoud, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 932 days.

(21) Appl. No.: 17/949,413

(22) Filed: Sep. 21, 2022

(65) Prior Publication Data

US 2023/0148938 A1 May 18, 2023

Related U.S. Application Data

(60) Provisional application No. 63/279,302, filed on Nov. 15, 2021.

(51) Int. Cl.

| | |
|---|---|
| ***A61B 5/352*** | (2021.01) |
| ***A61B 5/00*** | (2006.01) |
| ***A61B 5/29*** | (2021.01) |

(52) U.S. Cl.

CPC ................ *A61B 5/352* (2021.01); *A61B 5/29* (2021.01); *A61B 5/7221* (2013.01)

(58) Field of Classification Search

CPC ........... A61B 5/29; A61B 5/352; A61B 5/361; A61B 5/363; A61B 5/686; A61B 5/7203; A61B 5/7221

See application file for complete search history.

(56) References Cited

U.S. PATENT DOCUMENTS

2019/0336083 A1* 11/2019 Gill ........................ A61B 5/352

* cited by examiner

*Primary Examiner* — Amanda K Hulbert
(74) *Attorney, Agent, or Firm* — Dean D. Small; Carroll, Hoette & Butscher, LLC

(57) ABSTRACT

Computer implemented methods and implantable medical devices (IMD) are provided that obtain cardiac activity (CA) signals for a cardiac beat and compare the CA signals to a sensitivity level to detect a sensed event. One or more processors are configured to change the sensitivity level, utilized by the sensing circuitry, over the cardiac beat based on an adaptive sensitivity profile. The adaptive sensitivity profile has a maximum sensitivity limit (MSL). The process determines whether a characteristic of interest (COI) from a candidate event satisfies criteria relative to the COI for a collection of prior sensed events, declares the candidate event to be a valid sensed event or a false sensed event based on the determine operation; and adjusts the maximum sensitivity limit based on when the COI from the candidate event satisfies the criteria to provide adaptive sensing of CA signals.

10 Claims, 5 Drawing Sheets

METHOD AND SYSTEM TO MANAGE ADAPTIVE SENSING

CROSS-REFERENCE TO RELATED APPLICATIONS

This application claims priority to U.S. Provisional Patent Application No. 63/279,302, filed 15 Nov. 2021, titled "METHOD AND SYSTEM TO MANAGE ADAPTIVE SENSING". The subject matter of the provisional application is expressly incorporated herein by reference in its entirety.

FIELD OF THE INVENTION

Embodiments herein relate generally to implantable medical devices, and more particularly to manage adaptive sensing.

BACKGROUND OF THE INVENTION

Non-vascular implantable cardioverter defibrillators (NV-ICD) and more generally non-vascular implantable medical devices (NV-IMD) are utilized for various treatments. NV-IMDs are susceptible to high- and low-amplitude myopotential noise. If myopotentials are not identified correctly, this noise can cause device oversensing, leading to inappropriate therapy. Current noise detection algorithms can correctly identify high frequency, high amplitude noise, but experience difficulties with low frequency noise and low amplitude noise. Low frequency noise and low amplitude noise may be classified as an event of some type which causes incorrect sensing.

In general, IMDs include sensing circuitry that compares incoming electrical cardiac activity (CA) signals to a sensitivity level. When the CA signal amplitude exceeds the sensitivity level, the IMD declares some type of event (e.g., a P-wave, T-wave, R-wave, etc.). IMDs manage the sensitivity level in various ways, including the use of a sensitivity profile that changes the sensitivity level over time such that the instantaneous sensitivity level will differ at different points along a cardiac cycle.

An opportunity remains to improve the accuracy of event detection in IMDs experiencing difficulties with low frequency noise and low amplitude noise. Improved sensing algorithm performance could lead to reduced unnecessary data transmission to remote clinicians, episode review burden, and potentially prolong IMD longevity.

SUMMARY

In accordance with embodiments herein, an implantable medical device (IMD) is provided. The IMD comprises: electrodes configured to obtaining cardiac activity (CA) signals for a cardiac beat; sensing circuitry configured to compare the CA signals to a sensitivity level to detect a sensed event; memory to store specific executable instructions; and one or more processors configured to execute the specific executable instructions for: changing the sensitivity level, utilized by the sensing circuitry, over the cardiac beat based on an adaptive sensitivity profile, the adaptive sensitivity profile having a maximum sensitivity limit (MSL); determining whether a characteristic of interest (COI) from a candidate event satisfies criteria relative to the COI for a collection of prior sensed events; declaring the candidate event to be a valid sensed event or a false sensed event based on the determine operation; and adjusting the maximum sensitivity limit based on when the COI from the candidate event satisfies the criteria to provide adaptive sensing of CA signals.

Additionally, or alternatively, the COI represents amplitude, the sensed event represents an R-wave and the criteria includes an amplitude criteria for when the amplitude of a candidate R-wave is greater than or equal to a predetermined percentage of a mathematical combination of the amplitudes for a collection of prior R-waves. Additionally, or alternatively, the COI further represents R-R interval, and the criteria further includes an RR interval criteria for when an R-R interval of the candidate R-wave is less than or equal to a predetermined percentage of a mathematical combination of RR intervals for the collection of prior R-waves, the one or more processors further configured to apply the RR interval criteria only when the amplitude criteria is not satisfied. Additionally, or alternatively, the COI represents R-R interval, the sensed event represents an R-wave and the criteria includes an RR interval criteria for when an R-R interval of a candidate R-wave is less than or equal to a predetermined percentage of a mathematical combination of RR intervals for a collection of prior R-waves. Additionally, or alternatively, when the criteria is satisfied, the one or more processors further configured to adjust the maximum sensitivity limit by returning the maximum sensitivity limit to a baseline value and to save the candidate event as a valid sensed event. Additionally, or alternatively, the criteria include amplitude criteria and RR interval criteria and wherein, when the amplitude criteria is not satisfied and the RR interval criteria are satisfied, the one or more processors further configure to adjust the MSL by setting the maximum sensitivity limit to a MSL value based on a mathematical combination of the COI for the collection of prior sensed events and to declare the candidate event as the false sensed event. Additionally, or alternatively, the COI represents amplitude and the criteria include an amplitude criteria and an RR interval criteria, and wherein, when the amplitude and RR interval criteria are not satisfied, the one or more processors further configured to return to a last prior valid sensed event and return the maximum sensitivity limit to a baseline value. Additionally, or alternatively, the one or more processors are further configured to disable adjustment of the maximum sensitivity limit for a predetermined period of time to avoid ventricular arrhythmia under-sensing. Additionally, or alternatively, the one or more processors are further configured to repeat the comparing, determining, declaring and adjusting operations for multiple cardiac cycles and to detect an arrhythmia based on the valid sensed events detected for the multiple cardiac cycles. Additionally, or alternatively, the sensitivity level represents an instantaneous sensitivity level that the sensing circuitry compares to the CA signals, the instantaneous sensitivity level continuously varying over time and over a course of the cardiac beat.

In accordance with embodiments herein, a computer implemented method is provided to manage adaptive sensing by an implantable medical device (IMD). The method comprises: obtaining cardiac activity (CA) signals for a cardiac beat at implantable electrodes; utilizing sensing circuitry to compare the CA signals to a sensitivity level to detect a sensed event; and utilizing one or more processors, configured to execute the specific executable instructions for: changing the sensitivity level, utilized by the sensing circuitry, over the cardiac beat based on an adaptive sensitivity profile, the adaptive sensitivity profile having a maximum sensitivity limit (MSL); determining whether a characteristic of interest (COI) from a candidate event satisfies criteria relative to the COI for a collection of prior sensed events; declaring the candidate event to be a valid sensed event or a false sensed event based on the determine operation; and adjusting the maximum sensitivity limit based on when the COI from the candidate event satisfies the criteria to provide adaptive sensing of CA signals.

Additionally, or alternatively, the COI represents amplitude, the sensed event represents an R-wave and the criteria includes an amplitude criteria for when the amplitude of a candidate R-wave is greater than or equal to a predetermined percentage of a mathematical combination of the amplitudes for a collection of prior R-waves. Additionally, or alternatively, the COI further represents R-R interval, and the criteria further includes an RR interval criteria for when an R-R interval of the candidate R-wave is less than or equal to a predetermined percentage of a mathematical combination of RR intervals for the collection of prior R-waves, the one or more processors further configured to apply the RR interval criteria only when the amplitude criteria is not satisfied. Additionally, or alternatively, the COI represents R-R interval, the sensed event represents an R-wave and the criteria includes an RR interval criteria for when an R-R interval of a candidate R-wave is less than or equal to a predetermined percentage of a mathematical combination of RR intervals for a collection of prior R-waves. Additionally, or alternatively, when the criteria is satisfied, the method further comprising adjusting the maximum sensitivity limit by returning the maximum sensitivity limit to a baseline value and to save the candidate event as a valid sensed event. Additionally, or alternatively, the criteria include amplitude criteria and RR interval criteria and wherein, when the amplitude criteria is not satisfied and the RR interval criteria are satisfied, the method further comprising adjusting the MSL by setting the maximum sensitivity limit to a MSL value based on a mathematical combination of the COI for the collection of prior sensed events and to declare the candidate event as the false sensed event. Additionally, or alternatively, the COI represents amplitude and the criteria include an amplitude criteria and an RR interval criteria, and wherein, when the amplitude and RR interval criteria are not satisfied, the method further comprising returning to a last prior valid sensed event and returning the maximum sensitivity limit to a baseline value. Additionally, or alternatively, the method further comprises disabling adjustment of the maximum sensitivity limit for a predetermined period of time to avoid ventricular arrhythmia under-sensing. Additionally, or alternatively, the method further comprises repeating the comparing, determining, declaring and adjusting operations for multiple cardiac cycles and detecting an arrhythmia based on the valid sensed events detected for the multiple cardiac cycles. Additionally, or alternatively, the sensitivity level represents an instantaneous sensitivity level that the sensing circuitry compares to the CA signals, the instantaneous sensitivity level continuously varying over time and over a course of the cardiac beat.

DETAILED DESCRIPTION

Figure 1:
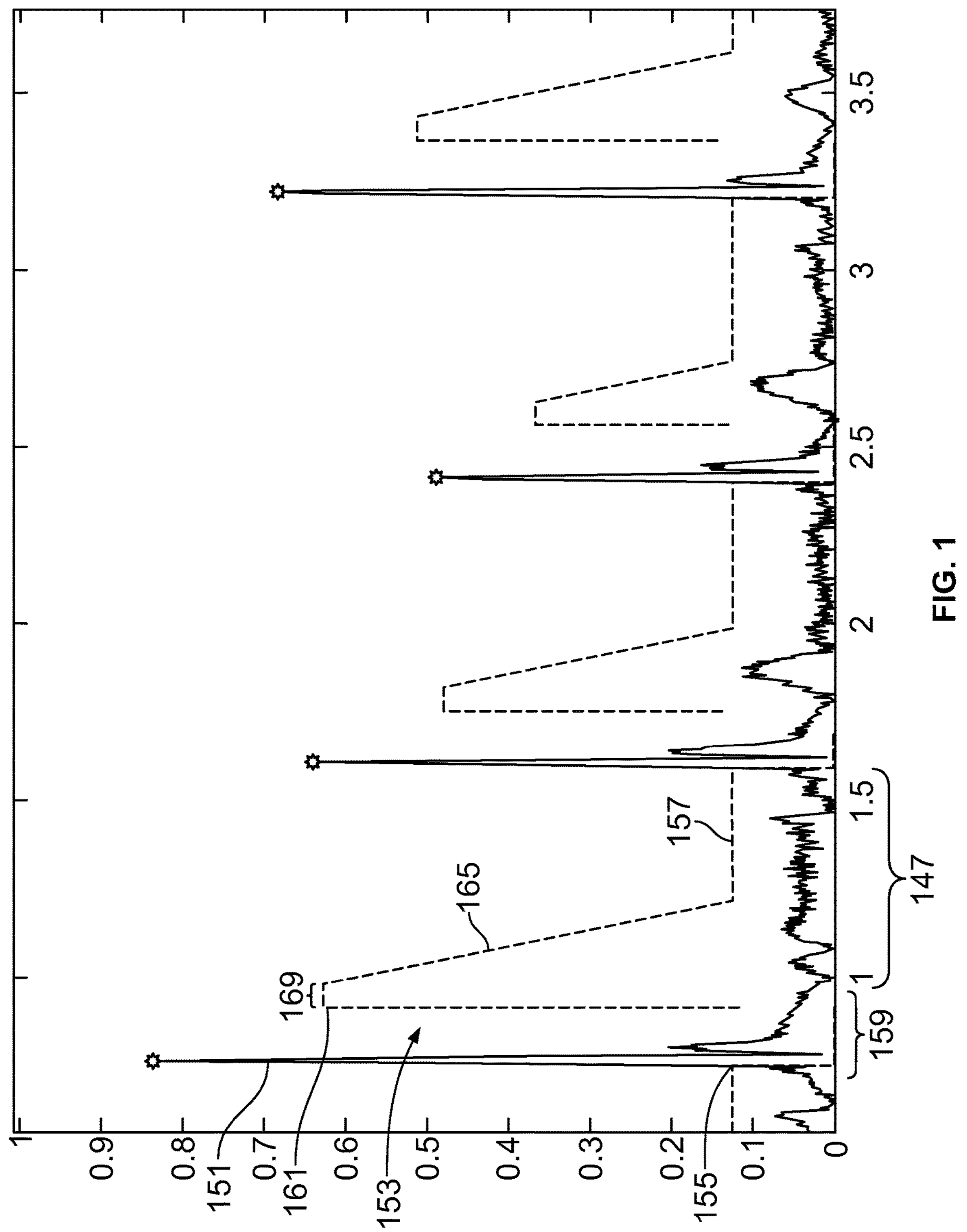
FIG. 1 illustrates an automatic sensing control (ASC) utilized by the sensing circuitry of the ICM to detect cardiac beats in accordance with embodiments herein.

The terms “cardiac activity signal”, “cardiac activity signals”, “CA signal” and “CA signals” (collectively “CA signals”) are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The term “marker” refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further non-limiting example, basic event markers may include “AF entry” to indicate a beginning of an AF event, “in AF” to indicate that AF is ongoing, “AF exit” to indicate that AF has terminated, “T” to indicate a tachycardia beat, “B” to indicate a bradycardia beat, “A” to indicate an asystole beat, “VS” to indicate a regular sinus beat, “Tachy” to indicate a tachycardia episode, “Brady” to indicate a Bradycardia episode, “Asystole” to indicate an asystole episode, “Patient activated” to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term “device documented marker” refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The term “COI” refers to a characteristic of interest within CA signals. Non-limiting examples of features of interest include an R-wave, P-wave, T-wave and isoelectric segments. A feature of interest may correspond to a peak of an individual R-wave, an average or median P, R or T-wave peak and the like.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The terms "correct", "true" and "valid", when used to refer to events, cardiac beats, R-waves and the like, shall mean events, cardiac beats, R-waves and the like that have been accessed based on the criteria described herein and satisfy the criteria. For example, a "correct", "true" and "valid" event, cardiac beat, R-wave and the like, is an event, cardiac beat, R-wave and the like that satisfies one or both of the amplitude criteria and RR interval criteria described herein.

The terms "incorrect", "false" and "invalid", when used to refer to events, cardiac beats, R-waves and the like, shall mean events, cardiac beats, R-waves and the like that have been accessed based on the criteria described herein and fail or do not satisfy one or both of the criteria. For example, an "incorrect", "false" or "invalid" event, cardiac beat, R-wave and the like, is an event, cardiac beat, R-wave and the like that does not satisfies one or both of the amplitude criteria and RR interval criteria described herein.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

The terms "refractory period" and "refractory interval" shall mean an interval following a paced or sensed event in a chamber of interest, during which the IMD is not reset and during which the IMD does not sense and does not respond to intrinsic events. For example, an atrial refractory period is triggered after an atrial sensed or paced event. During the atrial refractory period sensing is disabled over and atrial channel and events occurring in the atrial refractory period are not counted as intrinsic events.

The term "adaptive", as used in connection with a sensitivity profile, sensitivity limit, sensitivity level or other sensing parameters, refers to an ability of the processes herein to modify the value of sensitivity and/or sensing parameters based on features within the CA signals. The sensitivity profile parameters may include refractory period, start sensitivity, decay delay, sensitivity limit, slope of sensitivity decay, etc.

The term "sensitivity level", as used herein, refers to an instantaneous threshold that an input CA signal must exceed for an implantable device to identify a CA signal feature of interest (e.g., P-wave, R-wave). As one non-limiting example, software may be implemented using a programmed sensitivity level to declare an R-wave to be detected when the input CA signal exceeds the current programmed sensitivity level. In response, the software declares a device documented feature (e.g., R-wave) marker. The sensitivity level may be defined in various manners based on the nature of the CA signals. For example, when the CA signals measure electrical activity in terms of millivolts, the sensitivity level represents a millivolt threshold. For example, when a cardiac beat with a 0.14 mV amplitude is sensed by a device hardware, and R-wave may be detected when the current sensitivity level is programmed to 0.1 mV. However, when the sensitivity level is programmed to 0.15 mV or above, a cardiac beat with amplitude of 0.14 mV will not be detected as an R-wave.

System Overview

In accordance with embodiments herein, methods and devices are described to adjust a maximum sensitivity level (MSL) for an automatic sensitivity profile (ASP) in real-time and in a dynamic matter. The methods and devices take advantage of certain characteristics of interest in the detected events. More specifically, the methods and devices utilize peak R-wave amplitudes and R-R intervals detected in a rectified narrowband signal (VSENSE) to dynamically adjust a MSL parameter of the ASP in real-time. The methods and devices temporarily reprogram the ASC MSL for a series of beats and/or period of time when a COI from a candidate event satisfies a criteria relative to the same COI for a collection of prior events.

FIG. 1 illustrates an automatic sensing control (ASC) process utilized by the sensing circuitry of the IMD to detect cardiac beats in accordance with embodiments herein. FIG. 1 illustrates an example cardiac activity signal 151 after passing through a rectifier to convert all positive and negative deflections within the cardiac activity signal 151 to be positive deflections. The ASC process 670 manages the sensor circuit 680 to have an adaptive sensitivity profile 153 (denoted by a dashed line) that includes an instantaneous sensitivity level that varies over time and over the course of a cardiac beat.

FIG. 1 illustrates time along the horizontal axis and decreasing sensitivity along the vertical axis. The vertical axis represent voltage in a unit of interest, such as millivolts. Additionally, or alternatively, the vertical axis may represent a normalized scale from 0 to 1, where 0 represents total and complete sensitivity to all CA signal, while 1 represents complete insensitivity to any CA signals. An instantaneous sensitivity level of 0.1 along the vertical axis means that, when the CA signal amplitude exceeds 0.1 (e.g., 0.1 mV or 0.1 along a normalized scale), the sensing circuitry (and processor) will declare the CA signal to correspond to a "detected event" or "cardiac beat". Accordingly, the sensing circuity becomes "more sensitive" as the instantaneous sensitivity level approaches 0 and becomes "less sensitive" as the instantaneous sensitivity approaches 1.

The ASC process 670 begins with a sensing window 147 that is opened/activated at the expiration of a refractory interval 159. The refractory interval 159 runs for a predetermined time period (e.g., physician programmed or automatically determined by the IMD) that begins with a peak of an R-wave is detected. During the sensing window 147, the sensing circuitry adjusts the instantaneous sensitivity level to vary over time based on an adaptive sensitivity profile 153. The sensitivity profile 153 is defined by a set of parameters that include a threshold start sensitivity 161, decay delay parameter 169, maximum sensitivity limit (MSL) 157 and sensitivity decay 165. In the example of FIG. 1, the sensitivity decay 165 is linear with a constant slope. Additional or alternative parameters may be utilized to define a more complex or simpler profile. Optionally, the sensitivity decay 165 may be defined in accordance with a non-linear monotonically changing shape from the threshold start sensitivity 161 to the maximum sensitivity 157. The start sensitivity parameter defines a start sensitivity of the sensitivity profile. For example, the start sensitivity parameter may set start sensitivity to a percentage of the preceding R-wave peak amplitude. In the present example, the R-wave peak amplitude is 0.85 mV and accordingly, the level for the start sensitivity is approximately 0.75 mV (approximately 88% of the R-wave peak).

The refractory period/interval duration parameter defines a blanking interval beginning at a sensed R-wave, during which the processors and sensing circuitry do not search for events. For example, a T-wave may occur during the refractory period and is not detected as an event. The decay delay parameter defines the interval at which the sensitivity profile maintains the sensitivity level at a constant level following expiration of the refractory period before the sensitivity profile begins decreasing. When the sensitivity profile includes a linear sensitivity level decline, the decay delay rate defines a slope of the linear sensitivity level decline. In the present example, the slope of the sensitivity decay 165 is approximately 0.5 mV/0.5 second, although it is recognized that the slope may be steeper or shallower.

The maximum sensitivity limit defines a greatest sensitivity level (e.g., maximum resolution) that the instantaneous sensitivity level is allowed to reach. The MSL is utilized to avoid declaring events based on noise or in some instances cardiac activity that is not of interest.

In accordance new and unique aspects herein, the MSL is dynamically adjusted based on one or more COI from the cardiac cycle. As explained herein, the MSL is adjusted to maintain a desired relation to a peak of the R-wave for a preceding collection of heart beats (e.g., 50% of the average R-wave peak for the last 3 prior beats). It is recognized that the MSL may be adjusted based on a collection of more of fewer prior beats, based on a different mathematical combination of the prior R-waves and/or based on another COI other than the peak of the R-wave.

In accordance with the sensitivity profile 153, when the CA signal 151 crosses the sensitivity profile 153 at starting point 155, the ASC process 670 treats the point 155 as a sensed R-wave and begins a refractory interval 159. The sensing circuitry is disabled such that no new cardiac event (e.g., R-wave or T-wave) will be sensed during the refractory interval 159. At the end of the refractory interval 159, the sensing circuitry is enabled or activated and the instantaneous sensitivity level is adjusted/increased to the threshold start sensitivity 161. The threshold start sensitivity 161 may be defined as a percentage of the peak amplitude 163 of the QRS complex of the CA signal 151 detected during the refractory interval 159. The sensing circuit 680 maintains the threshold start sensitivity 161 for a decay delay parameter 169, after which the ASC process 670 begins to monotonically decrease the sensitivity (increase the resolution) of the sensing circuit 680 as denoted by the sensitivity decay 165 within the sensitivity profile 153. The sensing circuit 680 continues to decrease the sensitivity until either the sensitivity decay 165 reaches the maximum sensitivity 157 or an amplitude of the rectified cardiac activity signal 151 exceeds the sensor sensitivity profile 153, in which case the sensing circuitry 680 and processor 220 declare the point to represent a new sensed R wave.

The sensitivity of the sensing circuit 680 is continuously adjusted by the microcontroller 221 in accordance with the sensitivity profile 153 over time and over each cardiac beat. In one example, the sensing circuitry 224 may be implemented as an analogue circuit that compares analogue CA signals to an analogue threshold that defines the instantaneous sensitivity level, wherein the analogue threshold is continuously changed by the one or more processors. Additionally, or alternatively, the sensing circuitry 680 may represent digital circuitry that digitizes the CA signals into discrete CA signal samples and compares the CA signal samples to a digital threshold that defines the instantaneous sensitivity level, wherein the digital threshold is continuously changed by the one or more processors. For example, CA signals are generally sampled at a rate of 512 Hz and will obtain between 200 and 600 sample points during one cardiac beat. Over the course of one cardiac beat, at a heart rate of 60 bpm, the digital CA signals may include approximately 512 sample points. At a heart rate of 80 bpm, approximately 393 sample points would be obtained across one cardiac beat. At a heart rate of 100 bpm, approximately 307 sample points would be obtained across one cardiac beat. As a further example, the refractory period may be 160 ms to 250 ms. Depending upon the heart rate the CA signal may be compared to the sensitivity level over a period of time, following the refractory period for about 0.3 to 0.6 or more preferably 0.4 to 0.5 seconds.

Figures 2A, 2B:
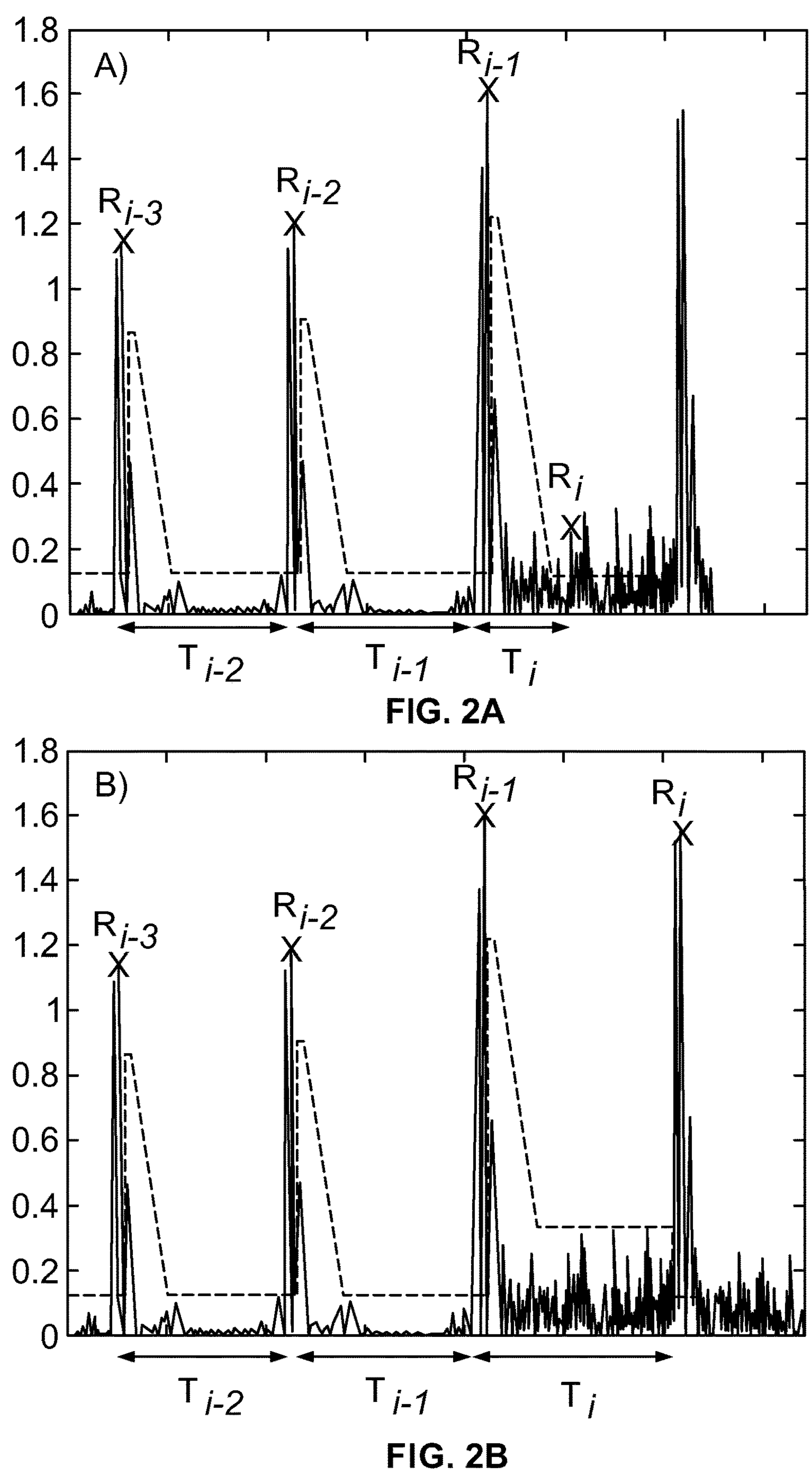
FIG. 2A illustrates an example ASC that would declare noise to be false cardiac events if a constant MSL were utilized.
FIG. 2B illustrates an example ASC utilizing a dynamically adaptive MSL that avoids declaring noise to be false cardiac events in accordance with embodiments herein.

FIG. 2A illustrates an example ASC that would declare noise to be false cardiac events if a constant MSL were utilized.

FIG. 2B illustrates an example ASC utilizing a dynamically adaptive MSL that avoids declaring noise to be false cardiac events in accordance with embodiments herein.

In FIGS. 2A and 2B, sensed events are labeled Ri-3, Ri-2, Ri-1 and Ri. The R-R intervals are labeled Ti-2, Ti-1 and Ti. FIG. 2A shows an example of an incorrectly detected sensed event Ri. Following the sensed event Ri-1, the CA signal experiences a substantial amount of noise. When the MSL is maintained at a constant level following the sensed event Ri-1, the sensing circuitry detects the noise to include one or more events at Ri. If left uncorrected, the false sensed event Ri would be treated as an R-wave and assigned a short RR interval Ti. If left uncorrected, the sensing circuitry could detect additional false R-waves which may be processed as an arrhythmia.

In accordance with embodiments herein, the ASC process determines whether a COI from a current candidate cardiac beat satisfies a criteria relative to the COI for a collection of prior cardiac beats and the ASC process adjusts the maximum sensitivity limit when the COI from the candidate cardiac beat satisfies the criteria to provide adaptive sensing of CA signals. For example, in accordance with embodiments herein, the COI represents amplitude and the cardiac beat represents an R-wave. In connection therewith, the criteria include an amplitude criteria for when the amplitude of a candidate R-wave is greater than or equal to a predetermined percentage of a mathematical combination of the amplitudes for a collection of prior R-waves.

With respect to FIG. 2B, the ASC process mathematically combines a predetermined number (e.g., three) of previous R wave amplitudes (Ri-3, Ri-2 and Ri-1) and adjusts the MSL to equal 50% of the median of the previous 3 correctly sensed events. Optionally, the MSL may be adjusted based on a different percentage a fixed numeric offset of the collection of prior sensed events. Optionally, the MSL may be adjusted based on a collection of two or more prior sensed events. In FIG. 2B, with the new MSL, the low level, slow noise does not trigger noise detection, and the correct R-wave is detected (Ri in FIG. 2B).

A time-out parameter is used to compare the previous collection of triggered sensed events. The R-R intervals are recorded and tracked for the last three correctly identified events. If Ti, R-R interval of the current event, is within a range of the previous three R-R intervals (e.g., if Ti is less than 125% of the median of Ti-3, Ti-2 and Ti-1) then the algorithm can increase the MSL to search for a correct sensed event. If Ti exceeds the threshold and does not meet the RR interval criteria, then the ASC process is disabled and the MSL is left at the nominal parameter for some predetermined period of time (i.e., 10 seconds) to avoid arrythmia under-sensing.

Figure 3:
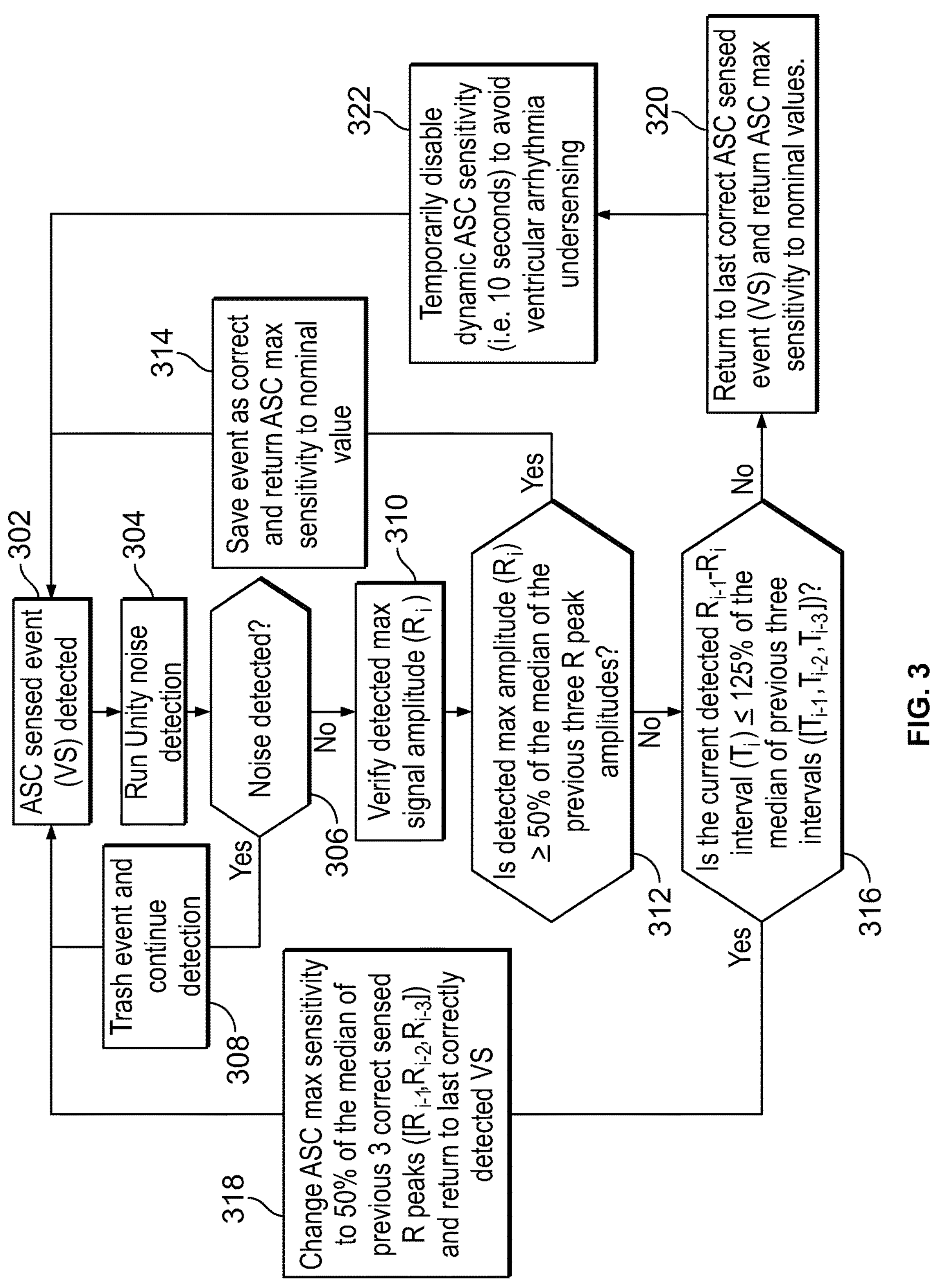
FIG. 3 illustrates an ASC process implemented in accordance with embodiments herein.

FIG. 3 illustrates a real-time ASC process implemented in accordance with embodiments herein. The operations of FIG. 3 may be implemented in whole or in part, in real-time, by one or more processors configured to execute specific executable instructions stored in memory of the IMD. Additionally, or alternatively, a portion of the operations of FIG. 3 may be implemented by hardware and/or firmware, such as in the sensing circuitry. At 302, the process of FIG. 3 may be initiate when the sensing circuitry detects a sensed event, such as a ventricular sensed (VS) event, also referred to as a peak of an R-wave. At 304, the one or more processors activate a noise detection process to verify if the sensed event is noise or a correctly sensed event. For example, the noise detection may determine how many turns (e.g., changes in direction) occur in the CA signals over a select window of time, that surpass a minimum threshold. Additionally, or alternatively, the CA signal may be integrated to determine an "area under the curve". Additionally, or alternatively, the CA signal may be otherwise analyzed for noise criteria.

At 306, the one or more processors determine whether noise was detected. If noise is detected, flow moves to 308, where the one or more processors "trash" the sensed event and the ASC process repeats for a next detected sensed event. If the sensed event is not classified as noise, then flow moves to 310. At 310 and 312, the one or more processors determine whether a COI from the candidate event satisfies criteria relative to the COI for a collection of prior sensed events. For example, the COI may represent amplitude, the sensed event may represent an R-wave and the criteria includes amplitude criteria for when the amplitude of a candidate R-wave is greater than or equal to a predetermined percentage of a mathematical combination of the amplitudes for a collection of prior R-waves. With respect to FIG. 2B, the operations at 310 and 312 verify a detected maximum signal amplitude (Ri) by comparing the peak amplitude to a mathematical combination of amplitudes for a collection of prior R-waves, such as the median of the previous three sensed R-wave peaks (Ri-3, Ri-2, Ri-1). At 312, if the amplitude of the current sensed event (Ri) is greater than 50% of the median of the previous three events, then the one or more processors accept the sensed event as true, and flow moves to 314.

At 314, the one or more processors save the candidate event as a valid sensed event and return the MSL to a baseline value (e.g., a nominal value). Flow returns to 302 to monitor for the next candidate event.

Returning to 312, when the one or more processors determine that the COI of the sensed event Ri does not meet the criterial (e.g, the amplitude criteria of greater than 50% of the median of the last 3 sensed events), then flow moves to 316 where an R-R interval (Ti) is verified.

At 316, the COI further represents R-R interval, and the criteria further includes RR interval criteria for when an R-R interval of the candidate R-wave is less than or equal to a predetermined percentage of a mathematical combination of RR intervals for the collection of prior R-waves. In the example of FIG. 3, the one or more processors further configured to apply the RR interval criteria only when the amplitude criteria is not satisfied. Additionally, or alternatively, the RR interval criteria may be applied even when the amplitude criteria is satisfied.

Figures 4, 5:
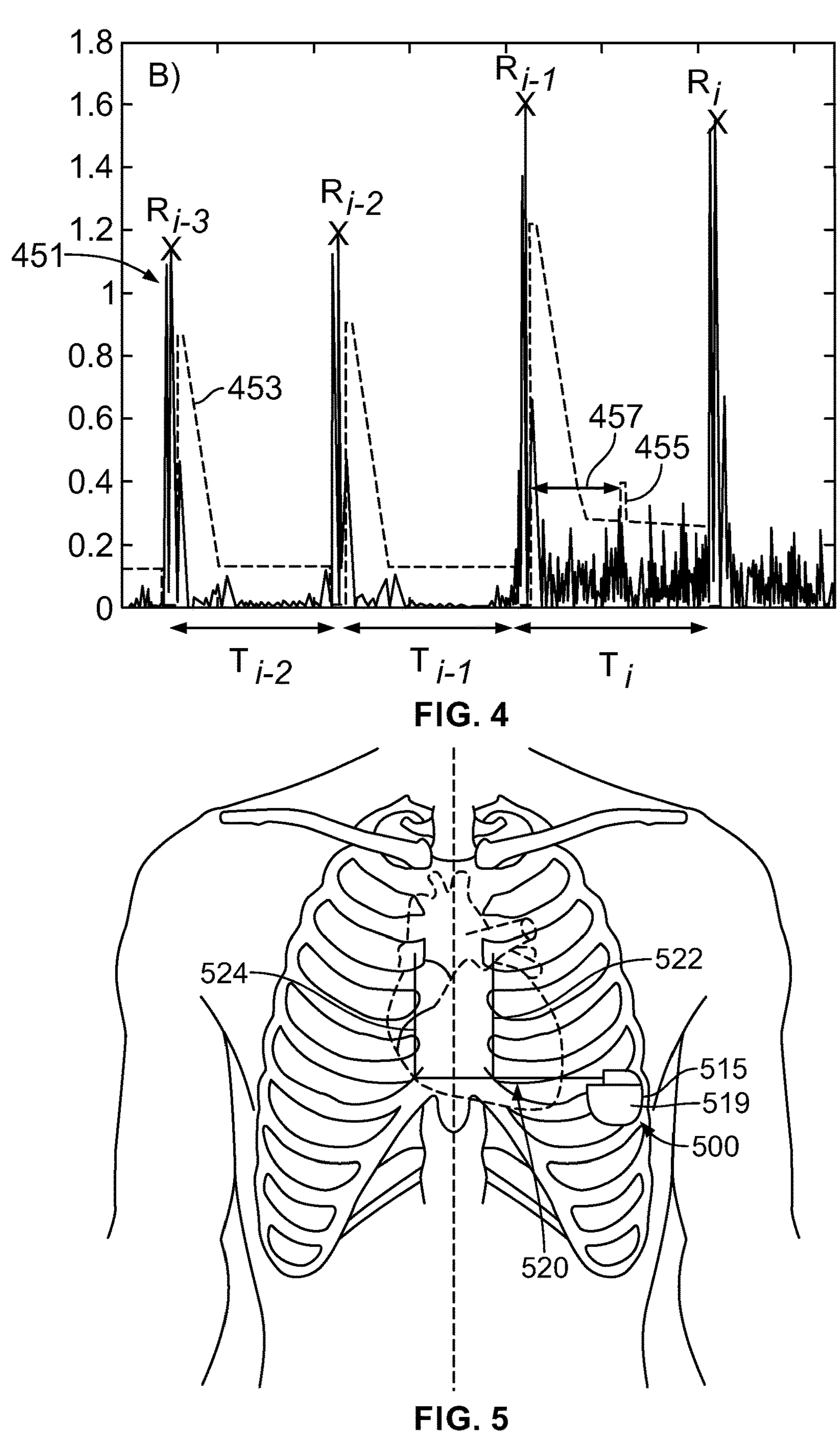
FIG. 4 illustrates an example implementation for RR interval criteria in accordance with embodiments herein.
FIG. 5 illustrates a torso of a patient to show the rib cage and a general outline of the heart and greater vessels.

FIG. 4 illustrates an example implementation for RR interval criteria in accordance with embodiments herein. FIG. 4 illustrates CA signals 451 and an adaptive sensitivity profile 453 that includes an instantaneous sensitivity level that varies over time and over the course of each cardiac beat. Sensed events Ri-3, Ri-2, Ri-1 are correctly detected and utilized to set various counters/timers within the IMD. Also, the sensed events Ri-3, Ri-2, Ri-1 are assigned markers to indicate the corresponding type of event that was detected (e.g., R-wave peaks). The markers may be utilized by various algorithms to detect arrhythmias, normal sinus rhythms and the like.

Following sensed event Ri-1 (FIG. 4), a candidate event may be declared at 455. The candidate event satisfies (at 312 in FIG. 3) the above discussed amplitude criteria (e.g., greater than 50% of the median R-wave amplitude). In the present example, the MSL is less than 50% of the 3 beat median R-wave amplitude. Accordingly, instances will arise where the candidate event 455 crosses the instantaneous sensitivity level but does not satisfy the amplitude criteria. The process next applies the RR interval criteria at 316. The candidate event 455 occurs a "candidate" interval 457 after the sensed event Ri-1. The interval 457 is referred to as a "candidate" interval as event 455 has not yet been declared to represent a R-wave sensed event. If the candidate interval 457 is less than 125% of a median of the previous collection of RR intervals (e.g., 3 RR intervals), then the candidate event 455 does not satisfy the RR interval criteria, and flow moves to 318. In the present example, the candidate interval 457 is too short to satisfy the RR interval criteria.

At 318, the one or more processors increase the MSL by a predetermined amount relative to a COI from the collection of prior sensed events. The criteria may include both amplitude criteria and RR interval criteria. When the amplitude criteria is not satisfied and the RR interval criteria are satisfied, the one or more processors are further configured to adjust the MSL by setting the maximum sensitivity limit to a MSL value based on a mathematical combination of the COI for the collection of prior sensed events and to declare the candidate event as the false sensed event. For example, the MSL may be set to equal 50% of the median of the last three R-wave amplitudes. Next the one or more processors returns a basis for any on-going monitoring and data collection operations to the last "correctly" detected sensed event. For example, any timers/counters that were set based on the last correct or valid sensed event continue to run and are not reset. As shown in FIG. 4, when the candidate event 455 is declared false, the last "correctly" detected sensed event represents event Ri-1. Accordingly, the RR interval, ventricular-atrial (VA) timer, and the like will continue to run and be measured from the sensed event Ri-1. The process repeats, and candidate event Ri is detected. The candidate event Ri passes the amplitude criteria at 312 and exhibits an RR interval Ti that is greater than 125% of the median of the 3 previous RR intervals Ti-3, Ti-2, Ti-1. Accordingly, flow moves to 320.

At 320, the one or more processors again return to the last correctly sensed event Ri-1, and also return the MSL to a baseline or nominal maximum sensitivity. At 322, the one or more processors further temporarily disable (i.e., 10 seconds) adjustment of the MSL for the adaptive sensitivity profile to avoid under-sensing ventricular arrhythmias. Flow returns to 302 where the next candidate event is analyzed. Thus, when the COI represents amplitude and the criteria include amplitude and RR interval criteria, and wherein, when the amplitude and RR interval criteria are not satisfied, the one or more processors further configured to return to a last prior valid sensed event and return the maximum sensitivity limit to a baseline value.

Implantable Medical Device

FIG. 5 illustrates a torso of a patient to show the rib cage and a general outline of the heart and greater vessels. In particular embodiments, the system may apply high voltage defibrillation shocks, as well as other general arrhythmia therapy, such as pacing therapy, cardiac resynchronization therapy (CRT), and the like. The system includes a subcutaneous implantable medical device (IMD) 514 that is configured to be implanted in a subcutaneous area exterior to the heart. In at least one embodiment, the system is entirely or fully subcutaneous. As shown in FIG. 5, the IMD 500 is positioned within a lateral region, such as along the left side of the rib cage under the left arm. The IMD 500 may be positioned relative to a vertical direction substantially aligned with the apex of the heart. The IMD 500 is configured to deliver various arrhythmia therapies, such as defibrillation therapy, pacing therapy, anti-tachycardia pacing therapy, cardioversion therapy, and the like. It is contemplated, however, that the system may include other components.

The lead 520 includes one or more electrodes 522, 524 that are used for providing electrical shock for defibrillation. Optionally, the lead 520 may include one or more sensing electrodes. A pulse generator 515 may be implanted subcutaneously and at least a portion of the lead 520 may be implanted subcutaneously. In particular embodiments, the IMD 500 is an entirely or fully subcutaneous IMD. The pulse generator 515 may be positioned at a lateral position or below an apex of the heart.

Figure 6:
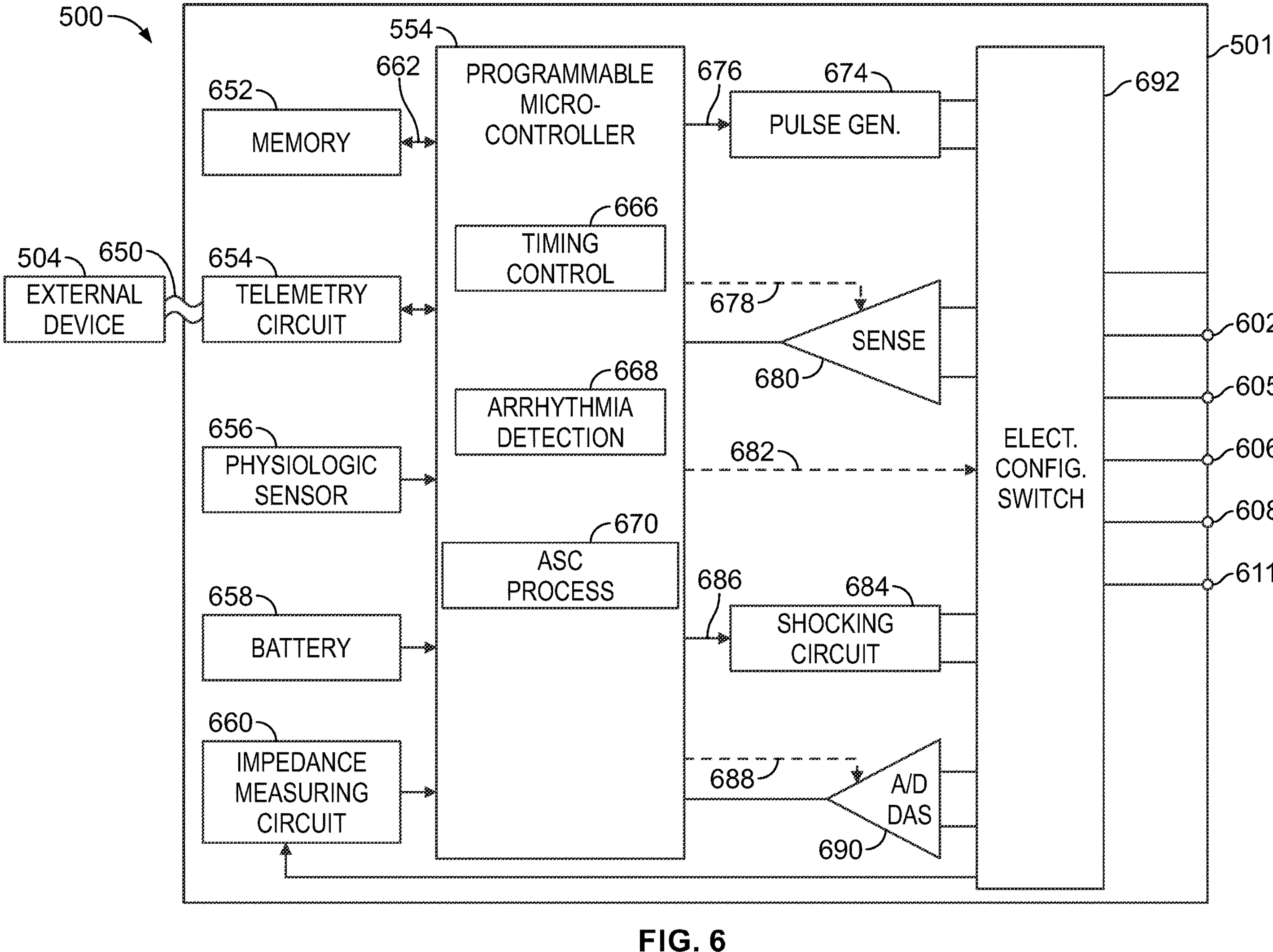
FIG. 6 illustrates a block diagram of the IMD 500 formed in accordance with embodiments herein.

FIG. 6 illustrates a block diagram of the IMD 500 formed in accordance with embodiments herein. The housing 501 (which is often referred to as the "can", "case", "encasing", or "case electrode") may be programmably selected to act as the return electrode for certain stimulus modes. Housing 501 further includes a connector (not shown) with a plurality of terminals 602, 605, 606, 608, and 611 configured to be connected to various combinations of electrodes. For example, the electrodes may include various combinations of ring, tip, coil and shocking electrodes and the like.

The IMD 500 includes a programmable microcontroller 664 that controls various operations of the IMD 500, including cardiac monitoring and stimulation therapy. Microcontroller 664 includes a microprocessor (or equivalent control circuitry), RAM and/or ROM memory, logic and timing circuitry, state machine circuitry, and I/O circuitry.

IMD 500 further includes a first chamber pulse generator 674 that generates stimulation pulses for delivery by one or more electrodes coupled thereto. The pulse generator 674 is controlled by the microcontroller 664 via control signal 676. The pulse generator 674 is coupled to the select electrode(s) via an electrode configuration switch 692, which includes multiple switches for connecting the desired electrodes to the appropriate I/O circuits, thereby facilitating electrode programmability. The switch 692 is controlled by a control signal 686 from the microcontroller 664.

Microcontroller 664 is illustrated to include timing control circuitry 666 to control the timing of the stimulation pulses (e.g., pacing rate, atrio-ventricular (AV) delay, atrial interconduction (A-A) delay, or ventricular interconduction (V-V) delay, etc.). The timing control circuitry 666 may also be used for the timing of refractory periods, blanking intervals, noise detection windows, evoked response windows, alert periods, marker channel timing, and so on. Microcontroller 664 also has an arrhythmia detector 668 for detecting arrhythmia conditions. Although not shown, the microcontroller 664 may further include other dedicated circuitry and/or firmware/software components that assist in monitoring various conditions of the patient's heart and managing pacing therapies. The timing control circuitry 666 may be configured to implement the processes described herein including adjustment of the alert period.

In a software or firmware-based implementation, the microcontroller 664 includes one or more processors that are configured to execute program instructions to further implement an ASC process 670 in accordance with embodiments herein. The ASC process directs one or more processors of the microcontroller to change the sensitivity level, utilized by the sensing circuitry 680, over the cardiac beat based on an adaptive sensitivity profile, the adaptive sensitivity profile having a maximum sensitivity limit (MSL); determine whether a characteristic of interest (COI) from a candidate event satisfies criteria relative to the COI for a collection of prior sensed events; declare the candidate event to be a valid sensed event or a false sensed event based on the determine operation; and adjust the maximum sensitivity limit based on when the COI from the candidate event satisfies the criteria to provide adaptive sensing of CA signals.

Additionally, or alternatively, the COI represents amplitude, the sensed event represents an R-wave and ASC process 670 applies, as the criteria, an amplitude criteria for when the amplitude of a candidate R-wave is greater than or equal to a predetermined percentage of a mathematical combination of the amplitudes for a collection of prior R-waves. Additionally, or alternatively, the COI further represents R-R interval, and the ASC process 670 applies, as a further criteria, an RR interval criteria for when an R-R interval of the candidate R-wave is less than or equal to a predetermined percentage of a mathematical combination of RR intervals for the collection of prior R-waves. Optionally, the one or more processors are further configured to apply the RR interval criteria only when the amplitude criteria is not satisfied. Additionally, or alternatively, when the criteria is satisfied, the one or more processors are further configured to adjust the maximum sensitivity limit by returning the maximum sensitivity limit to a baseline value and to save the candidate event as a valid sensed event.

In accordance with embodiments herein, the criteria include amplitude criteria and RR interval criteria and the ASC process 670 is configured such that, when the amplitude criteria is not satisfied and the RR interval criteria are satisfied, the one or more processors are further configure to adjust the MSL by setting the maximum sensitivity limit to a MSL value based on a mathematical combination of the COI for the collection of prior sensed events and to declare the candidate event as the false sensed event.

In accordance with embodiments herein, the COI may represent amplitude and the criteria include an amplitude criteria and an RR interval criteria, and the ASC process 670 implemented such that, when the amplitude and RR interval criteria are not satisfied, the one or more processors further configured to return to a last prior valid sensed event and return the maximum sensitivity limit to a baseline value. Additionally, or alternatively, the one or more processors are further configured to disable adjustment of the maximum sensitivity limit for a predetermined period of time to avoid ventricular arrhythmia under-sensing. Additionally, or alternatively, the one or more processors are further configured to repeat the compare, determine, declare and adjust operations for multiple cardiac cycles and to detect an arrhythmia based on the valid sensed events detected for the multiple cardiac cycles.

The IMD 500 includes sensing circuitry 680 selectively coupled to one or more electrodes that perform sensing operations, through the switch 692 to obtain cardiac activity (CA) signals for a cardiac beat and detect the presence of cardiac activity (CA) signals. The sensing circuitry 680 is configured to compare the CA signals to a sensitivity level to detect a sensed event within the CA signals. For example, the sensitivity level represents an instantaneous sensitivity level that the sensing circuitry compares to the CA signals, the instantaneous sensitivity level continuously varying over time and over a course of the cardiac beat. The sensing circuitry 680 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 692 determines the sensing polarity of the cardiac signal by selectively closing the appropriate switches. In this way, the clinician may program the sensing polarity independent of the stimulation polarity. The output of the sensing circuitry 680 is connected to the microcontroller 664 which, in turn, triggers or inhibits the pulse generator 674 in response to the absence or presence of cardiac activity. The sensing circuitry 680 receives a control signal 678 from the microcontroller 664 for purposes of controlling the gain, threshold, polarization charge removal circuitry (not shown), and the timing of any blocking circuitry (not shown) coupled to the inputs of the sensing circuitry.

In the example of FIG. 6, a single sensing circuit 680 is illustrated. Optionally, the IMD 500 may include multiple sensing circuit, similar to sensing circuit 680, where each sensing circuit is coupled to one or more electrodes and controlled by the microcontroller 664 to sense electrical activity detected at the corresponding one or more electrodes. The sensing circuit 680 may operate in a unipolar sensing configuration or in a bipolar sensing configuration. The IMD 500 further includes an analog-to-digital (ND) data acquisition system (DAS) 690 coupled to one or more electrodes via the switch 692 to sample cardiac signals across any pair of desired electrodes. The data acquisition system 690 is configured to acquire intracardiac electrogram signals, convert the raw analog data into digital data, and store the digital data for later processing and/or telemetric transmission to an external device 504 (e.g., a programmer, local transceiver, or a diagnostic system analyzer). The data acquisition system 690 is controlled by a control signal 688 from the microcontroller 664.

The microcontroller 664 is coupled to a memory 652 by a suitable data/address bus 662. The memory 652 (and/or firmware) may store one or more parameters that define the adaptive sensitivity profile. The adaptive sensitivity profile is defined by a set of parameters that include a threshold start sensitivity, decay delay parameter, maximum sensitivity limit (MSL) and sensitivity decay. The programmable operating parameters used by the microcontroller 664 are stored in memory 652 and used to customize the operation of the IMD 500 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The operating parameters of the IMD 500 may be non-invasively programmed into the memory 652 through a telemetry circuit 654 in telemetric communication via communication link 650 with the external device 504. The telemetry circuit 654 allows intracardiac electrograms and status information relating to the operation of the IMD 500 (as contained in the microcontroller 664 or memory 652) to be sent to the external device 504 through the established communication link 650.

The IMD 500 can further include one or more physiologic sensors 656. Such sensors are commonly referred to as "rate-responsive" sensors because they are typically used to adjust pacing stimulation rates according to the exercise state of the patient. However, the physiological sensor 656 may further be used to detect changes in cardiac output, changes in the physiological condition of the heart, or diurnal changes in activity (e.g., detecting sleep and wake states). Signals generated by the physiological sensors 656 are passed to the microcontroller 664 for analysis. The microcontroller 664 responds by adjusting the various pacing parameters (such as rate, AV Delay, V-V Delay, etc.) at which the atrial and ventricular pacing pulses are administered. While shown as being included within the unit 500, the physiologic sensor(s) 656 may be external to the unit 500, yet still be implanted within or carried by the patient. Examples of physiologic sensors might include sensors that, for example, sense respiration rate, pH of blood, ventricular gradient, activity, position/posture, minute ventilation (MV), and so forth.

A battery 658 provides operating power to all of the components in the IMD 500. The battery 658 is capable of operating at low current drains for long periods of time and is capable of providing high-current pulses (for capacitor charging) when the patient requires a shock pulse (e.g., in excess of 6 A, at voltages above 6 V, for periods of 50 seconds or more). The battery 658 also desirably has a predictable discharge characteristic so that elective replacement time can be detected. As one example, the unit 500 employs lithium/silver vanadium oxide batteries. The IMD 500 further includes an impedance measuring circuit 660, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 660 is coupled to the switch 692 so that any desired electrode may be used.

The IMD 500 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 664 further controls a shocking circuit 684 by way of a control signal 686. The shocking circuit 680 generates shocking pulses of low (e.g., up to 0.5 joules), moderate (e.g., 0.5-10 joules), or high energy (e.g., 11 to 40 joules), as controlled by the microcontroller 664. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Alternative IMDs

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. Patent Application having U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Additionally or alternatively, the IMD may implement one or more of the features and functions described in U.S. patent application Ser. No. 15/973,126, titled "METHOD AND SYSTEM FOR SECOND PASS CONFIRMATION OF DETECTED CARDIAC ARRHYTHMIC PATTERNS"; U.S. patent application Ser. No. 15/973,351, titled "METHOD AND SYSTEM TO DETECT R-WAVES IN CARDIAC ARRHYTHMIC PATTERNS"; U.S. patent application Ser. No. 15/973,307, titled "METHOD AND SYSTEM TO DETECT POST VENTRICULAR CONTRACTIONS IN CARDIAC ARRHYTHMIC PATTERNS"; and U.S. patent application Ser. No. 16/399,813, titled "METHOD AND SYSTEM TO DETECT NOISE IN CARDIAC ARRHYTHMIC PATTERNS", which is expressly incorporated herein by reference.

All references, including publications, patent applications and patents, cited herein are hereby incorporated by reference to the same extent as if each reference were individually and specifically indicated to be incorporated by reference and were set forth in its entirety herein.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:

electrodes configured to obtaining cardiac activity (CA) signals for cardiac beats;

sensing circuitry configured to compare the CA signals to a sensitivity level to detect sensed events, the sensed events including a collection of prior sensed events and a candidate sensed event;

memory to store specific executable instructions; and one or more processors configured to execute the specific executable instructions for:

changing the sensitivity level, utilized by the sensing circuitry, over the cardiac beats based on an adaptive sensitivity profile, the adaptive sensitivity profile having a maximum sensitivity limit (MSL);

determining whether at least one characteristic of interest (COI) from the candidate sensed event satisfies at least one criterion relative to the corresponding at least one COI for the collection of prior sensed events;

declaring the candidate sensed event to be a valid candidate sensed event or a false candidate sensed event based on the determining operation; and adjusting the MSL based on when the COI from the candidate sensed event satisfies the at least one criterion to provide adaptive sensing of CA signals.

2. The IMD of claim 1, wherein at least one the COI includes amplitude, the sensed events represent R-waves and the at least one criterion includes an amplitude criterion for when the amplitude of a candidate R-wave is greater than or equal to a predetermined percentage of a mathematical combination of the amplitudes for a collection of prior R-waves.

3. The IMD of claim 2, wherein the at least one COI further includes R-R interval, and the at least one criterion further includes an R-R interval criterion for when an R-R interval of the candidate R-wave is less than or equal to a predetermined percentage of a mathematical combination of R-R intervals for the collection of prior R-waves, the one or more processors further configured to apply the R-R interval criterion only when the amplitude criterion is not satisfied.

4. The IMD of claim 1, wherein the COI represents R-R interval, the sensed events represent R-waves and the at least one criterion includes an R-R interval criterion for when an R-R interval of a candidate R-wave is less than or equal to a predetermined percentage of a mathematical combination of R-R intervals for a collection of prior R-waves.

5. The IMD of claim 1, wherein, when the at least one criterion is satisfied, the one or more processors further configured to adjust the MSL by returning the MSL to a baseline value and to save the candidate sensed event as the valid candidate sensed event.

6. The IMD of claim 1, wherein the at least one criterion include an amplitude criterion and an R-R interval criterion and wherein, when the amplitude criterion is not satisfied and the R-R interval criterion is satisfied, the one or more processors further configure to adjust the MSL by setting the MSL to an MSL value based on a mathematical combination of the COI for the collection of the prior sensed events and to declare the candidate sensed event as the false candidate sensed event.

7. The IMD of claim 1, wherein the at least one criterion include an amplitude criterion and an R-R interval criterion, and wherein, when the amplitude and R-R interval criteria are not satisfied, the one or more processors further configured to return to a last prior valid candidate sensed event and return the MSL to a baseline value.

8. The IMD of claim 7, wherein the one or more processors are further configured to disable adjustment of the MSL for a predetermined period of time to avoid ventricular arrhythmia under-sensing.

9. The system of claim 1, wherein the one or more processors are further configured to repeat the comparing, determining, declaring and adjusting operations, in real-time, for multiple cardiac cycles and to detect an arrhythmia based on the valid sensed events detected for the multiple cardiac cycles.

10. The system of claim 1, wherein the sensitivity level represents an instantaneous sensitivity level that the sensing circuitry compares to the CA signals, the instantaneous sensitivity level continuously varying over time and over a course of the cardiac beat.

* * * * *